US00PP28285P2

(12) United States Plant Patent
Pieters

(10) Patent No.: US PP28,285 P2
(45) Date of Patent: Aug. 15, 2017

(54) ***CHRYSANTHEMUM* PLANT NAMED 'VEGA RED'**

(50) Latin Name: *Chrysanthemum×morifolium*
Varietal Denomination: Vega Red

(71) Applicant: Elien Sofie Pieters, Oostnieuwkerke (BE)

(72) Inventor: Elien Sofie Pieters, Oostnieuwkerke (BE)

(73) Assignee: Paraty B.V.B.A., Oostnieuwkerke (BE)

( * ) Notice: Subject to any disclaimer, the term of this patent is extended or adjusted under 35 U.S.C. 154(b) by 0 days.

(21) Appl. No.: 14/999,373

(22) Filed: Apr. 30, 2016

(51) Int. Cl.
*A01H 5/02* (2006.01)

(52) U.S. Cl.
USPC ..... Plt./293

(58) Field of Classification Search
USPC ..... Plt./293
CPC ..... A01H 5/0255
See application file for complete search history.

*Primary Examiner* — Kent L Bell
(74) *Attorney, Agent, or Firm* — C. A. Whealy

(57) ABSTRACT

A new and distinct cultivar of *Chrysanthemum* plant named 'Vega Red', characterized by its upright, outwardly spreading and uniformly rounded plant habit; moderately vigorous growth habit; freely branching habit; dense and full plant habit; dark green-colored leaves; uniform and freely flowering habit; and relatively large decorative-type inflorescences with deep red-colored ray florets that resist fading under full sunlight conditions.

1 Drawing Sheet

Botanical designation: *Chrysanthemum×morifolium.*
Cultivar denomination: 'VEGA RED'.

BACKGROUND OF THE INVENTION

The present invention relates to a new and distinct cultivar of *Chrysanthemum* plant, botanically known as *Chrysanthemum×morifolium* and hereinafter referred to by the name 'Vega Red'.

The new *Chrysanthemum* plant is a product of a planned breeding program conducted by the Inventor in Oostnieuwkerke, Belgium. The objective of the breeding program is to create new uniformly mounding and freely flowering *Chrysanthemum* plants with unique and attractive ray floret coloration.

The new *Chrysanthemum* plant originated from a cross-pollination made by the Inventor in Oostnieuwkerke, Belgium in September, 2010 of *Chrysanthemum×morifolium* 'PPP OLW 07', disclosed in U.S. Plant Pat. No. 20,393, as the female, or seed, parent with *Chrysanthemum×morifolium* 'Carpino Red', not patented, as the male, or pollen, parent. The new *Chrysanthemum* plant was discovered and selected by the Inventor as a flowering plant from within the progeny of the stated cross-pollination in a controlled greenhouse environment in Oostnieuwkerke, Belgium in September, 2011.

Asexual reproduction of the new *Chrysanthemum* plant by vegetative terminal cuttings was first conducted in a controlled greenhouse environment in Oostnieuwkerke, Belgium in January, 2012. Asexual reproduction by vegetative terminal cuttings has shown that the unique features of this new *Chrysanthemum* plant are stable and reproduced true to type in successive generations.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Vega Red'. These characteristics in combination distinguish 'Vega Red' as a new and distinct *Chrysanthemum* plant:

1. Upright, outwardly spreading and uniformly rounded plant habit; moderately vigorous growth habit.
2. Freely branching habit; dense and full plant habit.
3. Dark green-colored leaves.
4. Uniform and freely flowering habit.
5. Relatively large decorative-type inflorescences with deep red-colored ray florets that resist fading under full sunlight conditions.

Plants of the new *Chrysanthemum* differ from the female parent, 'PPP OLW 07', in the following characteristics:

1. Plants of the new *Chrysanthemum* are more compact than plants of 'PPP OLW 07'.
2. Plants of the new *Chrysanthemum* have smaller leaves than plants of 'PPP OLW 07'.
3. Plants of the new *Chrysanthemum* and 'PPP OLW 07' differ in ray floret color as inflorescences of plants of 'PPP OLW 07' have red-colored ray florets that fade under full sunlight conditions.

Plants of the new *Chrysanthemum* differ from the male parent, 'Carpino Red', in the following characteristics:

1. Plants of the new *Chrysanthemum* are larger than plants of 'Carpino Red'.
2. Plants of the new *Chrysanthemum* have larger inflorescences than plants of 'Carpino Red'.
3. Plants of the new *Chrysanthemum* and 'Carpino Red' differ in ray floret color as inflorescences of plants of 'Carpino Red' have darker red-colored ray florets.

Plants of the new *Chrysanthemum* can be compared to plants of *Chrysanthemum×morifolium* 'Helen Red', not patented. In side-by-side comparisons, Belgium, plants of the new *Chrysanthemum* differ from plants of 'Helen Red' in the following characteristics:

1. Plants of the new *Chrysanthemum* are more rounded than and not as upright as plants of 'Helen Red'.
2. Plants of the new *Chrysanthemum* are more flexible than and not as brittle as plants of 'Helen Red'.
3. Plants of the new *Chrysanthemum* and 'Helen Red' differ in ray floret color as inflorescences of plants of 'Helen Red' have red-colored ray florets that fade under full sunlight conditions.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant.

The photograph comprises a side perspective view of a typical flowering plant of 'Vega Red' grown in a container.

DETAILED BOTANICAL DESCRIPTION

The aforementioned photograph and following observations and measurements describe plants grown in 19-cm containers in an outdoor nursery in Oostnieuwkerke, Belgium during the summer and autumn and under cultural practices generally used in commercial *Chrysanthemum* production. During the production of the plants, day temperatures ranged from 20° C. to 25° C. and night temperatures ranged from 12° C. to 18° C. Plants were 20 weeks old when the photograph and description were taken. In the following description, color references are made to The Royal Horticultural Society Colour Chart, 2005 Edition, except where general terms of ordinary dictionary significance are used.

Botanical classification: *Chrysanthemum×morifolium* 'Vega Red'.

Parentage:

*Female, or seed, parent.*—*Chrysanthemum×morifolium* 'PPP OLW 07', disclosed in U.S. Plant Pat. No. 20,393.

*Male, or pollen, parent.*—*Chrysanthemum×morifolium* 'Carpino Red', not patented.

Propagation:

*Type.*—Vegetative terminal cuttings.

*Time to initiate roots, summer.*—About 14 days at temperatures about 20° C.

*Time to initiate roots, winter.*—About 20 days at temperatures about 20° C.

*Time to produce a rooted young plant, summer.*—About 30 days at temperatures about 20° C.

*Time to produce a rooted young plant, winter.*—About 40 days at temperatures about 20° C.

*Root description.*—Fine, fibrous; typically light brown in color, actual color of the roots dependent on substrate composition, water quality, fertilizer, substrate temperature and age of roots.

*Rooting habit.*—Freely branching; medium density.

Plant description:

*Appearance.*—Perennial decorative-type *Chrysanthemum*; stems upright and outwardly spreading giving a uniformly rounded appearance to the plant; plants nearly spherical in overall shape; very freely branching habit, about 25 primary lateral branches develop, each primary lateral branch with multiple secondary branches; pinching enhances lateral branch development; dense and full plant habit; moderately vigorous growth habit; medium growth rate.

*Plant height.*—About 35 cm.

*Plant width.*—About 50 cm.

*Lateral branches.*—Length: About 25 cm. Diameter: About 2 mm to 3 mm. Internode length: About 2.5 cm. Strength: Strong, flexible. Aspect: Upright to outwardly spreading. Texture: Pubescent; longitudinally ridged. Luster: Matte. Color: Close to 136A.

*Leaves.*—Arrangement: Alternate, simple. Length: About 2.5 cm to 4.5 cm. Width: About 1.5 cm to 3 cm. Apex: Rounded to cuspidate. Base: Attenuate. Margin: Palmately lobed and serrate, sinuses between lateral lobes divergent to parallel. Texture, upper and lower surfaces: Slightly pubescent. Luster, upper and lower surfaces: Matte. Color: Developing leaves, upper surface: Close to 139C. Developing leaves, lower surface: Close to 137D. Fully expanded leaves, upper surface: Close to N137C; venation, close to 148C. Fully expanded leaves, lower surface: Close to 147B; venation, close to 147B to 147C. Petioles: Length: About 1 cm. Diameter: About 2 mm. Texture, upper and lower surfaces: Slightly pubescent; slightly rough. Luster, upper and lower surfaces: Matte. Color, upper surface: Close to 146C. Color, lower surface: Close to 146D.

Inflorescence description:

*Appearance.*—Decorative-type inflorescence form; inflorescences borne on terminals above foliar plane; disc and ray florets arranged acropetally on a capitulum.

*Fragrance.*—Faintly fragrant, pungent.

*Flowering time.*—Under natural season conditions, plants flower in early September in Belgium.

*Postproduction longevity.*—Inflorescences maintain good color and substance for about five weeks on the plant grown in an outdoor nursery; inflorescences persistent.

*Quantity of inflorescences.*—Freely flowering habit with about 20 inflorescences developing per lateral branch with numerous inflorescences developing per plant.

*Inflorescence buds.*—Height: About 8 mm. Diameter: About 1.2 cm. Shape: Globular. Texture: Smooth. Color: Close to 144A and 137C.

*Inflorescence size and shape.*—Diameter: Relatively large, about 5 cm. Depth (height): About 4 cm. Disc diameter: About 1.5 mm.

*Receptacles.*—Diameter: About 3 mm. Height: About 2.5 mm to 3 mm. Shape: Circular; raised dome. Texture: Smooth, glabrous. Color: Close to 144B.

*Ray florets.*—Quantity and arrangement: About or more than 125 to 150 ray florets per inflorescence arranged in about eight whorls. Length: About 3.5 cm to 5 cm. Width: About 7 mm. Shape: Oval. Apex: Rounded. Base: Attenuate. Margin: Entire. Aspect: Mostly flat. Texture, upper and lower surfaces: Smooth, glabrous. Luster, upper and lower surfaces: Matte. Color: When opening and fully opened, upper surface: Close to 53A; color does not fade with development nor under full sunlight conditions.

When opening and fully opened, lower surface: Close to 185B; color does not fade with development.

*Disc florets*.—Quantity and arrangement: About 150 disc florets per inflorescence and spirally massed at the center of the receptacle. Length: About 3 mm. Diameter: About 0.5 mm to 1 mm. Shape: Tubular, elongated; apices acute. Texture: Smooth, glabrous. Color: Apex: Close to 144C; becoming closer to 12A with development. Mid-section: Close to 5B. Base: Close to 145D.

*Phyllaries*.—Quantity and arrangement: About 25 phyllaries per inflorescence arranged in about two or three whorls. Length: About 4 mm to 6 mm. Width: About 2 mm to 3 mm. Shape: Ovate. Apex: Rounded. Base: Rounded to truncate. Margin: Entire. Texture, upper and lower surfaces: Smooth, glabrous. Luster, upper and lower surfaces: Matte. Color, upper surface: Close to 137A. Color, lower surface: Close to N137B.

*Peduncles*.—Length, terminal peduncle: About 4 cm. Length, fourth peduncle: About 6 cm. Length, seventh peduncle: About 8 cm. Diameter: About 2 mm. Angle: About 30° from vertical. Strength: Moderately strong. Texture: Slightly pubescent. Luster: Matte. Color: Close to 146B.

*Reproductive organs*.—Androecium: None observed. Gynoecium: None observed.

*Seeds and fruit*.—Seed and fruit production have not been observed on plants of the new *Chrysanthemum*.

Disease & pest resistance: Resistance to pathogens and pests common to *Chrysanthemum* plants has not been observed on plants of the new *Chrysanthemum* grown under commercial production conditions.

Garden performance: Plants of the new *Chrysanthemum* have demonstrated excellent garden performance and will tolerate temperatures ranging from about 0° C. to about 45° C.

It is claimed:

1. A new and distinct *Chrysanthemum* plant named 'Vega Red' as illustrated and described.

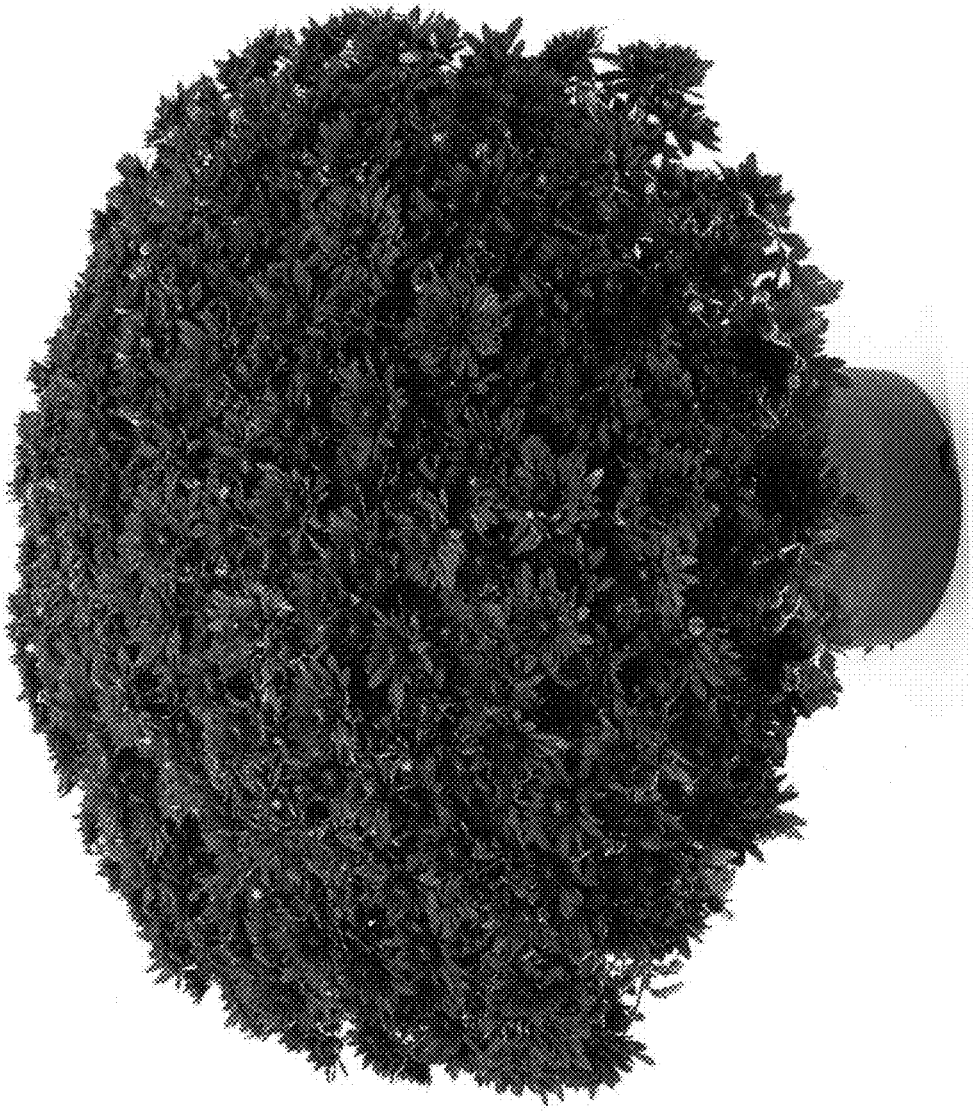

* * * * *